United States Patent [19]

Frohning et al.

[11] Patent Number: 4,956,328
[45] Date of Patent: Sep. 11, 1990

[54] PROCESS FOR THE PREPARATION OF CATALYST COMPOSITIONS CONTAINING NICKEL, ALUMINA, AND ZIRCONIUM DIOXIDE AND CATALYSTS MADE THEREFROM

[75] Inventors: Carl D. Frohning, Wesel; Gerhardt Horn, Oberhausen, both of Fed. Rep. of Germany

[73] Assignee: Hoechst Aktiengesellschaft, Fed. Rep. of Germany

[21] Appl. No.: 325,661

[22] Filed: Mar. 20, 1989

[30] Foreign Application Priority Data

Mar. 31, 1988 [DE] Fed. Rep. of Germany ....... 3811038

[51] Int. Cl.$^5$ .................. B01J 21/04; B01J 21/06; B01J 23/74
[52] U.S. Cl. .................. 502/242; 502/185; 502/335
[58] Field of Search .................. 502/185, 242, 335

[56] References Cited

U.S. PATENT DOCUMENTS

| 2,564,331 | 8/1951 | Hawley | 252/472 |
| 3,186,957 | 6/1965 | Stiles | 502/335 |
| 4,307,248 | 12/1981 | Barnett et al. | 564/358 |
| 4,384,985 | 5/1983 | Crum et al. | 252/437 |
| 4,657,889 | 4/1987 | Ganguli et al. | 502/335 |
| 4,687,568 | 8/1987 | Kukes et al. | 208/251 H |

FOREIGN PATENT DOCUMENTS

| 97047 | 12/1983 | European Pat. Off. . | |
| 1384329 | 3/1988 | U.S.S.R. | 502/335 |
| 2066690 | 7/1981 | United Kingdom . | |

Primary Examiner—W. J. Shine
Attorney, Agent, or Firm—Jordan B. Bierman

[57] ABSTRACT

A process for the preparation of a compound comprising precipitation from an aqueous solution of a mixture of nickel, aluminum, and zirconium salts by means of an aqueous precipitating solution. The latter contains an amount of a basic compound which is in stoichiometric excess of that required for complete precipitation of the salts. The precipitation is carried out at at least 60° C. and a pH of 7 to 10. A catalyst which is the product of the foregoing process, as well as its use in the hydrogenation of nitriles, aromatic hydrocarbons, nitro compounds, and/or olefins is also disclosed.

70 Claims, No Drawings

PROCESS FOR THE PREPARATION OF CATALYST COMPOSITIONS CONTAINING NICKEL, ALUMINA, AND ZIRCONIUM DIOXIDE AND CATALYSTS MADE THEREFROM

The present invention is directed to a method of preparing a catalyst comprising nickel, alumina, and zirconium dioxide for use in a variety of hydrogenation reactions. The catalyst made by the process and the use thereof are also a part of the present invention.

BACKGROUND OF THE INVENTION

USSR Patent No. 28 31 85 describes catalysts composed of nickel, aluminum oxide, and zirconium dioxide. These catalysts are prepared by precipitating nickel and aluminum oxide onto zirconium dioxide, which constitutes the support.

Nickel-zirconium dioxide catalysts are described in U.S. Pat. No. 2,564,331. Therein, an aqueous solution of zirconium sulfate is added to an aqueous solution of sodium carbonate, the latter being present in large excess. A basic zirconium compound is precipitated which redissolves due to the excess of carbonate ions. Thereafter, aqueous nickel sulfate is added at about 74° C. and a mixed precipitate consisting of nickel-zirconium carbonate is formed. This is further processed by washing, drying, calcination, and reduction.

A process for the preparation of catalysts by simultaneous precipitation of metals in the form of their insoluble oxalates is taught in U.S. Pat. No. 3,876,557. The pH value is maintained at 1.0 to 3.0 and a wide variety of metals are indicated as being useful. Specifically, nickel, cobalt, iron, copper, zinc, zirconium, aluminum, barium, calcium, strontium, and magnesium are all named specifically.

DE AS 12 57 753 sets forth the preparation of zirconium dioxide-activated nickel catalyst which is formed by the precipitation of insoluble carbonates. Ammonia and carbon dioxide are evaporated from a solution of ammonium zirconyl carbonate and nickel ammine carbonate sufficiently to ensure that a mixture of basic carbonates precipitates out at about 82° C. or higher. After filtration, the mixture is dried, calcined and reduced.

When catalyst compositions consisting of two or three components are prepared by precipitation, care must be taken to make sure that the precipitation leads to as homogeneous a mixture of the individual components as possible. The afore-mentioned processes do not give sufficient guarantee of this.

According to the procedure described in the US-PS 2,564,331 a large excess of carbonate is used. This means that initially pure nickel carbonate is precipitated and the actual mixed precipitation only takes place within a narrow range whilst towards the end of the precipitation only zirconium carbonate is deposited.

If the processes described in the US-PS 3,867,557 and the DE-AS 12 57 753 are followed, a gradual shifting of the pH value during precipitation is achieved, on the one hand, by adding an aqueous oxalic acid solution to a metal mixed-salt solution and, on the other hand, by evaporating ammonia and carbon dioxide.

As the solubility of the individual components greatly depends on the prevailing pH value, the mixture which is precipitated always correlates with the pH value. As the precipitated mixture changes its composition as a function of the pH value, differently composed, inhomogeneous precipitated mixtures are obtained due to the change in the pH value.

As these difficulties already occur when only two components—e.g. nickel and zirconium compounds—are precipitated, it must be assumed that precipitation of homogeneous coprecipitates consisting of three metal compounds must fulfil special requirements. It is the purpose of the present invention to solve this problem.

BRIEF DESCRIPTION OF THE INVENTION

The present invention is directed to a process for the preparation of a nickel, aluminum oxide, and zirconium oxide catalyst composition by coprecipitation, filtration, drying, and reduction. The three metals are precipitated simultaneously from an aqueous salt solution thereof by mixing with an excess of an aqueous solution of a basic compound. The precipitation takes place at a temperature of 60° C. or higher and a pH value of 7 to 10.

DETAILED DESCRIPTION OF THE INVENTION

The present invention is a process for the preparation of a catalyst comprising precipitation of the catalyst from an aqueous starting solution which is a mixture of nickel, aluminum, and zirconium salts. The starting solution is mixed with an aqueous precipitating solution containing a basic compound. The compound is present in a stoichiometric excess over that which is required for complete precipitation of the salts. The reaction is carried out at a precipitation temperature of at least 60° C. and a precipitation pH of 7 to 10.

It is to be preferred that the stoichiometric excess of the basic compound be from 5% to 100% and the process carried out at a precipitation temperature of 60° C. to 120° C.

Undesired hydrolysis may be prevented by the inclusion of an excess of free acid in the starting solution. More specifically, it is advantageous to maintain an acid ratio of $H^+$ to $Zr^{4+}$ of 2:1 to 40:1. This ratio is determined by titration of the starting solution with sodium hydroxide to a pH value of 0.8. It has been found more desirable to maintain the acid ratio at 3:1 to 30:1, and most preferable to maintain it at 4:1 to 20:1. Preferred free acids are hydrochloric acid, sulfuric acid, and nitric acid, with nitric acid being most preferable.

The starting solution usefully comprises 10 to 100, in particular to 20 to 80, preferably 30 to 50 grams of nickel per liter. It exhibits aluminum corresponding to 1 to 30, in particular 3 to 15, preferably 4 to 10 parts by weight of $Al_2O_3$ per 100 parts by weight of nickel. Furthermore, it contains zirconium corresponding to 0.5 to 20, n particular 1 to 10, preferably 1.5 to 5 parts by weight of $ZrO_2$ per 100 parts by weight of nickel.

The starting solution is prepared by dissolving water-soluble inorganic, organic or complex salts of nickel, zirconium and aluminum in water. Well suited salts are the sulfates, chlorides, acetates, propionates, butyrates and nitrates. It has proved particularly valuable to use nickel, aluminum and zirconium in the form of their sulfates, chlorides, acetates and nitrates, preferably in the form of their nitrates.

An aqueous solution of a basic compound, especially an aqueous alkali metal carbonate, alkali metal hydrogen carbonate, alkali metal hydroxide, ammonium hydroxide or ammonium carbonate solution serves as a precipitating solution.

Mixtures of the same can also be used. An aqueous solution containing sodium carbonate and/or sodium bicarbonate is particularly suitable. The precipitating solution desirably has a pH of 7.5 to 13. A pH of 8 to 12 is considered better, and 9 to 11 is most preferable.

The concentration of the basic compound can vary substantially. However, 0.1 to 4.0 equivalents of the basic compound per liter of precipitating solution has been found advantageous. More preferably is 0.6 to 3.0 equivalents of the basic compound per liter and 1.6 to 2.4 equivalents of the basic compound per liter are considered yto be most preferable. However, when alkali metal carbonate is used, very good results have been obtained with aqueous solutions having 0.3 to 1.5 moles of carbonate per liter of solution, preferably 0.8 to 1.2 moles per liter.

It will be appreciated that obtaining a homogeneous coprecipitate is of great importance in obtaining the best possible catalyst in accordance with the present invention. Therefore, it is advisable to use a substantial excess of the basic compound; hence, a stoichiometric excess of 5 to 100% of basic compound is recommended. An excess of 10 to 70% has been found more useful, and it is especially desirable to use 20 to 40% excess. In all cases, the excess is based upon the amount of basic compound needed to completely precipitate the nickel, aluminum, and zirconium salts in the starting solution.

The amount of stoichiometric excess is determined so that a homogenous catalyst precipitates and the metal salts are precipitated quantitatively. The reaction is begun simply by continuously mixing the starting solution with the precipitating solution or, in a preferred embodiment of the invention, adding the starting solution to the precipitating solution. The latter is especially convenient since the feed rate of only a single solution need be monitored.

It is also preferred that the catalyst be precipitated onto a support. The support material can be fed into the reaction along with the starting solution and/or the precipitating solution. This is especially desirable in the case of the addition of the starting solution to the precipitating solution.

Another extremely advantageous modification of the process comprises mixing the starting solution and the precipitating solution with one another and, thereafter, adding the support. It has been found that, if this variant is used, the catalyst composition obtained has physical properties (e.g. mechanical stability and apparent density), which facilitate further processing.

As the support, such materials as activated carbon, clay, pumice, α-alumina, silica, silica gel, and siliceous earths are all suitable. In particular, reference is made to silica, silica gel, kieselguhr, siliceous earth, and mixtures thereof. Most desirable are kieselguhr and silica which is preferably used in the form of precipitated silicic acid.

While the particular size of the support material is not particulaarly critical. The support material has a particle size of 0.1 to 200 μm, preferably, 0.5 to 50 μm and, most preferably, 1 to 30 μm. The amount of support material may be varied within wide limits. Per 100 parts by weight of nickel, 6 to 80 parts by weight of support material have been found satisfactory. Particularly, 15 to 65 parts per 100 parts of nickel have been used. It is most preferable to use 35 to 50 parts by weight of support material per 100 parts by weight of nickel.

In order to obtain the more desirable homogeneous coprecipitates of the present invention, the pH range during precipitation is maintained between 7 and 10. If especially homogeneous precipitates are required, the pH range should be 7.3 to 9; most preferably is 7.5 to 8.5. In general, it is recommended that substantial fluctuations in pH during precipitation be avoided. This can be achieved most simply by steady addition of the starting solution to the precipitating solution. At the same time, the addition should not be too rapid.

The temperature should be at least 60° C. and substantially higher temperatures can be used, especially if the precipitation is carried out under pressure. In general, a temperature range of 60° to 120° C. is suitable. Better results can be obtained between 70° and 110° C., while best results are found between 95° and 105° C. Since the precipitation temperature has an influence on the size of the particles and their apparent density, it is desirable to keep the temperature as constant as possible.

At the same time, it will be recognized that the temperature selected for precipitation will be governed by the physical properties of the desired ultimate catalyst composition. Since the precipitation occurs substantially quantitatively, the composition of the precipitated mixture corresponds closely to the ratios of salts found in the starting solution.

When precipitation is complete, the mixture is cooled to temperatures of 70° C. or below, and the precipitate is filtered out of the mother liquor. Thereafter, the precipitate is washed, dried, and reduced. Of course, if particular shapes are appropriate, it may be molded as desired. In addition, the catalysts composition can be stabilized as, for example, by selective treatment with air or oxygen.

The undesired soluble impurities are removed from the catalyst composition by washing with water. It is recommended that the residual content of the basic compound should correspond to less than 1% $Na_2O$. This figure is preferably 0.5% and, most preferably, 0.2%, all by weight. Thereafter, the composition may be molded after being washed.

The drying step is preferably carried out in increasing elevated temperature stages. Suitable temperatures can be between 40° and 120° C., particularly 50° to 100° C. This will insure that the residual moisture is less than 10% by weight based upon the total catalyst composition.

The reduction step is usefully performed using hydrogen at 300° to 550° C. For good results, a reduction of at least 80% should be achieved. It is better if at least 90% is reached, and best if at least 95% is obtained. It will be appreciated that the higher degrees of reduction produce more reactive catalyst compositions. The degree of reduction is the proportion of nickel metal to the total nickel content multiplied by 100%.

With regard to the catalysts of the present invention, it has been known in the past that nickel-containing catalyst can be modified by the addition of either zirconium dioxide or alumina. Each of these two promoters has a favorable effect on hydrogenation reactions. However, despite the foregoing, which can be prepared by coprecipitation of nickel and alumina and coprecipitation of nickel and zirconium dioxide, there remains a demand for catalysts with even more improved properties.

The present catalyst compositions are surprisingly superior to those previously known. In particular, the presence of 20 to 90% by weight of nickel, based on the catalyst composition, along with 1 to 30 parts by weight of alumina and 0.5 to 20 parts by weight of zirconium dioxide, in each case per 100 parts by weight of nickel, have been found extremely suitable. More particularly, the use of 35 to 75% by weight of nickel and most preferably 40 to 70% by weight of nickel are worthy of particular mention.

Particle sizes of the support materials ranging from 0.1 to 200 µm, particularly 0.5 to 50 µm, and preferably 1.0 to 30 µm are especially desirable. The various clays, activated carbon, pumice, alumina, silica, silica gel, kieselguhr, and siliceous earths are eminently suitable as support materials. Silica, silica gel, kieselguhr, and siliceous earth are particularly suitable, with kieselguhr and silica, in the form of precipitated silicic acid, are most desirable.

The advantages of the catalyst of the present invention can be achieved even when the proportions of the different components are varied. Such compositions as 35 to 75% by weight of nickel based on the total catalyst composition, 3 to 15 parts by weight of alumina per 100 parts by weight of nickel, and 1 to 10 parts by weight of zirconium dioxide per 100 parts by weight of nickel have been found particularly useful.

Still more favorable are compositions having 40 to 70% by weight of nickel, based on the catalyst composition, 4 to 10 parts by weight of alumina per 100 parts by weight of nickel, and 1.5 to 5 parts by weight of zirconium dioxide per 100 parts by weight of nickel. Even though smaller amounts of alumina and zirconium dioxide are present, these compositions possess properties which correspond very favorably to those previously set forth.

The catalysts of the present invention are particularly useful in the liquid phase hydrogenation of nitriles, aromatic hydrocarbons, nitro compounds, and olefins. The catalysts are sufficiently active so that moderate temperatures of 50° to 140° C. can be used with resulting high conversions and excellent selectivity. The superiority of the present catalysts as compared with those containing nickel and alumina or nickel and zirconium dioxide is apparent. In addition to the foregoing, the present catalyst compositions are extremely stable.

The following examples are intended to illustrate the present invention but are not to be taken as being limitative.

EXAMPLE 1

Preparation of a catalyst composition containing 100 parts by weight of nickel, 6.5 parts by weight of $Al_2O_3$, 1.5 parts by weight of $ZrO_2$, and 45 parts by weight of kieselguhr.

305.76 g of $Ni(NO_3)_2.6H_2O$ and 29.52 g of $Al(NO_3)_3.9H_2O$ are dissolved in 1760 ml of distilled water. Separately, 2.32 g of zirconium carbonate (with a zirconium content corresponding to 39.8% by weight of $ZrO_2$) is dissolved in 9 ml of technical nitric acid (56% by weight of $HNO_3$). The desired mixed-salt starting solution is obtained by combining these two solutions. The precipitating solution is prepared by dissolving 147.04 g of $Na_2CO_3$ in 1416 ml of distilled water; the solution contains 104 g of $Na_2CO_3$/liter.

The mixed-salt starting solution is heated to 101° C. and the precipitating solution to 100° C., then the hot mixed-salt starting solution is poured steadily into the vigorously stirred precipitating solution over a period of three minutes. 27.76 g of kieselguhr are stirred into the freshly precipitated suspension and the mixture thus formed is stirred for another three minutes.

Then the mother liquor is separated from the precipitated product by filtration, and the precipitated product is washed with distilled water having a temperature of 70° C. until the alkali content of the washing water is 20 mg of $Na_2O$/liter near the end. The filter cake is suspended in 70° C. hot distilled water (ratio of filter cake to distilled water=1:1) for further processing. The mixture is stirred for about 60 minutes and then refiltered. The filter cake then formed is extruded as cylindrical shapes (diameter 5 mm, length 8 to 15 mm) and then dried at increasing temperatures (50° to 75° C.) with air until the residual water content is less than 10 weight % based on the dried mass. The dried material is reduced in a $H_2$ stream (400 liters of $H_2$ per liter of catalyst per hour) at 470° C. The reduction is complete after 4 hours. The catalyst composition contains about 63% by weight of nickel and exhibits a degree of reduction of 99%. By treatment with an $O_2/N_2$ gas mixture (the temperature of the catalyst composition should not exceed 100° C.), the pyrophoric catalyst is converted to a stabilized form which is insensitive to air.

EXAMPLE 2

Preparation of a catalyst composition containing 100 parts by weight of nickel, 5 parts by weight of $Al_2O_3$, 3 parts by weight of $ZrO_2$ and 45 parts by weight of kieselguhr.

305.76 g of $Ni(NO_3)_2.6H_2O$ and 22.68 g of $Al(NO_3)_3.9H_2O$ are dissolved in 1760 ml of distilled water. Separately 4.656 g of zirconium carbonate (with a zirconium content corresponding to 39.8 wt. % of $ZrO_2$) is dissolved in 18 ml of technical nitric acid (56 wt. % of $HNO_3$). The desired mixed-salt starting solution is obtained by combining these two solutions. The precipitating solution is prepared by dissolving 175.2 g of $Na_2CO_3$ in 1680 ml of distilled water. The solution contains 104 g of $Na_2CO_3$/liter.

Then the same procedure as in Example 1 is followed, the mixed-salt starting solution is heated to 101° C. and the precipitating solution to 100° C. The hot mixed-salt starting solution is then poured steadily into the vigorously stirred precipitating solution over a period of three minutes. 27.76 g of kieselguhr are stirred into the freshly precipitated suspension and the mixture thus formed is stirred for another three minutes.

Then, as described in Example 1, the mixture is filtered, washed, suspended in distilled water, refiltered, extruded, dried, reduced with $H_2$ and optionally stabilized with an $O_2/N_2$ gas mixture.

EXAMPLES 3a to 3c

Hydrogenation of nitrobenzene 394 g of nitrobenzene and 150 g of water are reacted in the presence of 0.95 g of catalyst in a 1-liter autoclave with stirring at 30 bar $H_2$ pressure and a temperature of 130° C. The results obtained using various catalysts are to be found in Table 1 below.

TABLE 1

| Example | 3a | 3b (comp.) | 3c (comp.) |
|---|---|---|---|
| catalyst[1]: | | | |
| Ni | 100 | 100 | 100 |
| $Al_2O_3$ | 5 | 8 | — |
| $ZrO_2$ | 3 | — | 8 |
| $SiO_2$ | 45 | 45 | 45 |
| reaction time (min)[2] | 90 | 115 | 180 |
| reaction product[3]: | | | |

TABLE 1-continued

| Example | 3a | 3b (comp.) | 3c (comp.) |
|---|---|---|---|
| cyclohexylamine | 0.17 | 1.3 | 0.8 |
| aniline | 99.8 | 97.6 | 95.3 |
| byproducts[4] | 0.03 | 2.1 | 3.9 |
| nitrobenzene | — | — | 0.2 |

[1]Figures in parts by weight, prepared as described in Example 2.
[2]End of the $H_2$ take-up
[3]Figures in % by weight determined by gas chromatographic analysis
[4]e.g. azobenzene, azoxybenzene and hydrazobenzene

EXAMPLES 4a to 4c

Hydrogenation of aromatic hydrocarbons 400 g of a hydrocarbon mixture (proprietary product Esso Varsol: boiling range 140° to 170° C., aromatics content 24.3 wt. %) is reacted in the presence of 3.3 g of catalyst in a 1-liter autoclave with stirring at 20 bar $H_2$ pressure and a temperature of 140° C.

The results using various catalysts are given in Table 2 below.

TABLE 2

| Example | 4a | 4b (comp.) | 4c (comp.) |
|---|---|---|---|
| catalyst[1] | I | II | III |
| reaction time (min) | 100 | 125 | 195 |
| aromatics part | <1 ppm | 3 ppm | 37 ppm |

[1]Compare figures in table 1

EXAMPLES 5a to 5b

Hydrogenation of nitriles to primary amines 300 g of tallow fatty acid nitrile (iodine number 51) is mixed with catalyst and 17.5 g of $NH_3$, and reacted in a 1-liter autoclave with stirring at 30 bar ($H_2+NH_3$) pressure and 135° C. 1.0 g of catalyst I is used in Example 5a and 2.5 g of catalyst II in Example 5b (comparison). The results of the tests are given in Table 3.

TABLE 3

| Example | 5a | 5b (comp.) |
|---|---|---|
| catalyst[1] | I | II |
| reaction time (min)[2] | 150 | 145 |
| reaction product[3] | | |
| primary amine | 95.5 | 90.5 |
| sec. and tert. amine | 4.3 | 8.5 |
| iodine number | 49 | 50 |

[1]Compare figures in Table 1
[2]End of the $H_2$ take-up
[3]Figures in % by weight determined by gas chromatographic analysis

What we claim is:

1. A process for the preparation of a composition comprising precipitation from an aqueous starting solution of a mixture of nickel, aluminum, and zirconium salts by means of an aqueous precipitating solution containing an amount of a basic compound, said amount being in stoichiometric excess of that required for complete precipitation of said salts, said precipitation being carried out at a precipitation temperature of at least 60° C. and a precipitation pH of 7 to 10, and depositing said composition onto a support.

2. The process of claim 1 wherein said stoichiometric excess is 5% to 100%.

3. The process of claim 1 wherein said precipitation temperature is 60° to 120° C.

4. The process of claim 1 wherein said starting solution contains a starting excess of free acid.

5. The process of claim 4 wherein said starting solution contains said free acid in an acid ratio of $H^+$ to $Zr^{4+}$ of 2:1 to 40:1, as determined by titration with NaOH to an end point of 0.8.

6. The process of claim 5 wherein said acid ratio is 3:1 to 30:1.

7. The process of claim 6 wherein said acid ratio is 4:1 to 20:1.

8. The process of claim 4 wherein said free acid is HCl, $H_2SO_4$, or $HNO_3$.

9. The process of claim 8 wherein said free acid is $HNO_3$.

10. The process of claim 1 wherein said starting solution comprises 10 to 100 grams of nickel per liter of said starting solution, 1 to 30 parts by weight of alumina per 100 parts of nickel, and 0.5 to 20 parts by weight of zirconium dioxide per 100 parts of nickel.

11. The process of claim 10 wherein said starting solution comprises 20 to 80 grams of nickel per liter of said starting solution, 3 to 15 parts by weight of alumina per 100 parts of nickel, and 1 to 10 parts by weight of zirconium dioxide per 100 parts of nickel.

12. The process of claim 11 wherein said starting solution comprises 30 to 50 grams of nickel per liter of said starting solution, 4 to 10 parts by weight of alumina per 100 parts of nickel, and 1.5 to 5 parts by weight of zirconium dioxide per 100 parts of nickel.

13. The process of claim 1 wherein said salts are organic, inorganic, or complex.

14. The process of claim 1 wherein said salts are sulfates, chlorides, acetates, propionates, butyrates, and/or nitrates.

15. The process of claim 14 wherein said salts are sulfates, acetates, and/or nitrates.

16. The process of claim 15 wherein said salts are nitrates.

17. The process of claim 1 wherein said basic compound is an alkali metal carbonate, alkali metal hydrogen carbonate, alkali metal hydroxide, ammonium hydroxide, and/or ammonium carbonate.

18. The process of claim 17 wherein said basic compound is sodium carbonate and/or sodium bicarbonate.

19. The process of claim 1 wherein said precipitating solution has a solution pH of 7.5 to 13.

20. The process of claim 19 wherein said precipitating solution has a solution pH of 8 to 12.

21. The process of claim 20 wherein said precipitating solution has a solution pH of 9 to 11.

22. The process of claim 1 wherein said precipitating solution contains 0.1 to 4.0 equivalents of said basic compound per liter of said precipitating solution.

23. The process of claim 1 wherein said composition contains 100 parts by weight of nickel, about 6.5 parts by weight of alumina, about 1.5 parts by weight of zirconium, and about 45 parts by weight of kieselguhr.

24. The process of claim 22 wherein said precipitating solution contains 0.6 to 3.0 equivalents of said basic compound per liter of said precipitating solution.

25. The process of claim 24 wherein said precipitating solution contains 1.6 to 2.4 equivalents of said basic compound per liter of said precipitating solution.

26. The process of claim 22 wherein said basic compound is an alkali metal carbonate and said precipitating solution contains 0.3 to 1.5 equivalents thereof per liter of said precipitating solution.

27. The process of claim 26 wherein said precipitating solution contains 0.8 to 1.2 moles per liter of said precipitating solution.

28. The process of claim 2 wherein said stoichiometric excess is 10% to 70%.

29. The process of claim 28 wherein said stoichiometric excess is 20% to 40%.

30. The process of claim 1 wherein said starting solution and said precipitating solution are brought together and mixed.

31. The process of claim 30 wherein said starting solution is added to said precipitating solution.

32. The process of claim 1 wherein said support is suspended in said starting solution and/or said precipitating solution.

33. The method of claim 1 wherein said starting solution is mixed with said precipitating solution and said support is added thereafter.

34. The process of claim 1 wherein said support is activated carbon, clay, pumice, gamma-alumina, silica, silica gel, kieselguhr, siliceous earths, or mixtures thereof.

35. The process of claim 34 wherein said support is kieselguhr and/or silica, in the form of precipitated silicic acid.

36. The process of claim 1 wherein said support has a particle size of 0.1 to 200 μm.

37. The process of claim 36 wherein said particle size is 0.5 to 50 μm.

38. The process of claim 37 wherein said particle size is 1 to 30 μm.

39. The process of claim 1 wherein there is 6 to 80 parts by weight of said support per 100 parts of nickel.

40. The process of claim 39 wherein there is 15 to 65 parts by weight of said support per 100 parts of nickel.

41. The process of claim 40 wherein there is 35 to 50 parts by weight of said support per 100 parts of nickel.

42. The process of claim 1 wherein said precipitation pH is 7.3 to 9.

43. The process of claim 42 wherein said precipitation pH is 7.5 to 8.5.

44. The process of claim 3 wherein said precipitation temperature is 70° to 110° C.

45. The process of claim 44 wherein said precipitation temperature is 95° to 105° C.

46. The process of claim 1 wherein said composition is thereafter cooled, filtered, washed, dried, and reduced to produce a catalyst.

47. The process of claim 46 wherein said composition is molded after being washed.

48. The process of claim 46 wherein said catalyst is stabilized by selective treatment with air or oxygen.

49. The process of claim 46 wherein said composition is washed until it contains water-soluble impurities corresponding to less than 1% by weight $Na_2O$.

50. The process of claim 49 wherein said composition is washed until it contains water-soluble impurities corresponding to less than 0.5% by weight $Na_2O$.

51. The process of claim 50 wherein said composition is washed until it contains water-soluble impurities corresponding to less than 0.2% by weight $Na_2O$.

52. The process of claim 46 wherein said composition is dried at 40° to 120° C.

53. The process of claim 52 wherein said composition is dried at 50° to 100° C.

54. The process of claim 46 wherein said composition is reduced in the presence of hydrogen at 300° to 550° C.

55. The process of claim 46 wherein said composition is reduced to a degree of reduction of at least 80%.

56. The process of claim 55 wherein said degree of reduction is at least 90%.

57. The process of claim 56 wherein said degree of reduction is at least 95%.

58. The process of claim 46 wherein said composition, after drying, contains less than 10% water, based on its total composition.

59. A composition which is the product of the process of claim 1.

60. The composition of claim 59 wherein there is 20% to 90% by weight of nickel based on said catalyst, 1 to 30 parts by weight of alumina per 100 parts of nickel, and 0.5 to 20 parts by weight of zirconium dioxide per 100 parts of nickel on said support.

61. The composition of claim 60 wherein there is 35% to 75% by weight of nickel based on said catalyst.

62. The composition of claim 61 wherein there is 40% to 70% by weight of nickel based on said catalyst.

63. The composition of claim 61 wherein there are 3 to 15 parts by weight of alumina per 100 parts of nickel and 1 to 10 parts by weight of zirconium dioxide per 100 parts of nickel.

64. The composition of claim 62 wherein there are 4 to 10 parts by weight of alumina per 100 parts of nickel and 1.5 to 5 parts by weight of zirconium dioxide per 100 parts of nickel.

65. A composition which is the product of the process of claim 34.

66. A composition which is the product of the process of claim 35.

67. A composition which is the product of the process of claim 36.

68. A composition which is the product of the process of claim 37.

69. A composition which is the product of the process of claim 38.

70. The process of claim 1 for the preparation of a catalyst composition containing nickel, aluminum oxide, and zirconium oxide, wherein said stoichiometric excess is 5% to 100% and said precipitation temperature is 60° to 120° C.

* * * * *